Feb. 16, 1932.
R. L. CATRON
Plant Pat. 6
HYBRID TEA ROSE
Filed Nov. 15, 1930
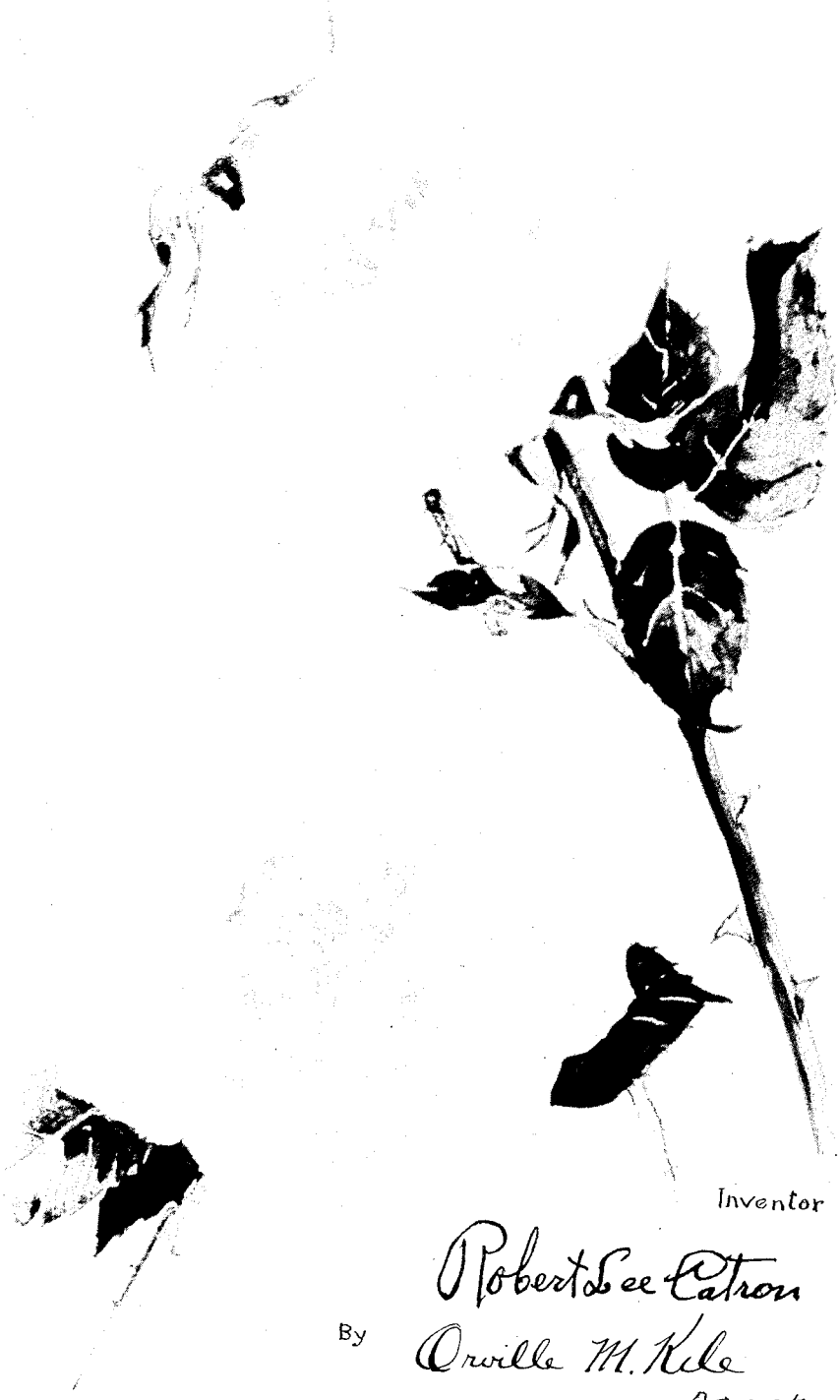
Inventor
Robert Lee Catron
By Orville M. Kile
Agent Patented Feb. 16, 1932

Plant Pat. 6

UNITED STATES PATENT OFFICE

ROBERT LEE CATRON, OF RICHMOND, INDIANA, ASSIGNOR TO THE JOSEPH H. HILL COMPANY, OF RICHMOND, INDIANA, A CORPORATION

HYBRID TEA ROSE

Application filed November 15, 1930. Serial No. 496,002.

My invention relates to improvements in fragrant, pink, hybrid tea roses. The objects of my improvements are to provide a rose of the type mentioned, having a truer shade of pink, long buds, a flower which, when half opened, gives a distinctive Gardenia-like effect, and a rose having superior keeping qualities.

This new rose is the result of definite breeding efforts carried on by myself and my associates and originated through the crossing of the variety Rapture on Souvenir de Claudius Pernet. The improved seedling was first discovered about the year 1929 and has since been propagated and developed. It is briefly described on page 220 of the 1930 edition of the American Rose Annual, published by the American Rose Society, editorial offices Harrisburg, Pennsylvania.

The accompanying illustrations show in full color and in approximately natural size, a bud, a half opened flower and a fully opened flower of my new variety.

The following is a detailed description of this rose:

A bush or upright rose, of medium height (4 to 6 feet), very vigorous in growth and of free blooming habit.

Stem stoutish, green, beset with stoutish, greenish, beak-shaped, sharp-pointed spines or prickles, retrorsely directed, straight or slightly curved above; the upper stem or peduncle bearing the flower, straightish or moderately curved, scarcely zigzag.

Leaves on flower-bearing stems 4 to 5 inches long, glabrous, the petioles bearing scattered glandular hairs, leaflets 3 to 5 (on the second to fifth leaves), ovate, rather closely dentate, the teeth often subulate at tip.

Stipules 3/8 to 1/2 inch long, 1/8 to 3/16 inches wide, adnate to the petiole and terminating in slender, subulate, bristle-like, ascending, or somewhat spreading, points averaging 1/8 inch in length.

Hips in the bud stage and during the opening of the flower about 3/8 to 1/2 inch in length, somewhat oblanceolate, tapering gradually downward into stem or peduncle, longer and more tapering than in related varieties having approximately the same petalage.

Buds long, ovate-lanceolate, pointed, about 1 1/4 to 1 1/2 inches long, being longer and more pointed than in related varieties having about the same petalage.

Sepals normally 5, about 1 to 1 and 1/4 inches long in the unopened bud, oblanceolate, acuminate to long-acuminate, usually bearing two slender teeth, one on either side near the middle, the sepal tip developing into a more or less leaf-like, oblanceolate or elliptical appendage, 1/2 to two inches or more in length, with coarsely-toothed margins.

The opening bud 1 1/2 to 2 inches long, the petals regularly arranged and upright giving a Gardenia-like effect; the petals broadly obovate or sub-orbiculate in shape, 24–26 (averaging 25) in number, pink, rose color to deep rose pink, becoming rose pink or thulite pink with age, (of the Ridgway color scale), the color fairly uniformly distributed over surface, except for the yellowish base; the flower semi-double to approaching double, with high center, 4 or 4 1/2 to 5 inches in spread when fully opened, and of superior keeping quality.

I claim:

A rose as herein shown and described, characterized chiefly by its true rose pink color, long buds, superior keeping qualities, and a flower which when half-opened gives a distinctive Gardenia-like effect.

ROBERT LEE CATRON.